(12) United States Patent
Mayenberger

(10) Patent No.: US 6,290,196 B1
(45) Date of Patent: Sep. 18, 2001

(54) HOLDING DEVICE FOR A SURGICAL INSTRUMENT

(75) Inventor: Rupert Mayenberger, Rielasingen (DE)

(73) Assignee: Aesculap AG & Co. KG, Tuttlingen (DE)

( * ) Notice: Subject to any disclaimer, the term of this patent is extended or adjusted under 35 U.S.C. 154(b) by 0 days.

(21) Appl. No.: 09/307,671

(22) Filed: May 10, 1999

(30) Foreign Application Priority Data

May 16, 1998 (DE) .............................................. 198 22 195

(51) Int. Cl.$^7$ .............................. E04G 3/00; B25J 17/00; B66C 1/00
(52) U.S. Cl. ................................... 248/274.1; 248/123.2; 248/281.1; 74/490.06; 414/729; 414/735
(58) Field of Search ........................... 248/274.1, 288.31, 248/281.11, 323, 654, 123.11; 414/729–730; 74/490.06

(56) References Cited

U.S. PATENT DOCUMENTS

| | | | |
|---|---|---|---|
| 4,684,088 | * 8/1987 | Heller | 248/123.2 |
| 4,741,607 | * 5/1988 | Heller | 359/384 |
| 4,806,068 | * 2/1989 | Kohli et al. | 414/735 |
| 4,881,709 | * 11/1989 | Nakamura | 248/281.1 |
| 4,976,582 | * 12/1990 | Clavel | 414/729 |
| 5,351,925 | * 10/1994 | Druais | 248/325 |
| 5,715,729 | * 2/1998 | Toyama et al. | 74/490.03 |
| 5,813,287 | * 9/1998 | McMurtry et al. | 74/490.06 |

FOREIGN PATENT DOCUMENTS 482 439    2/1968   (CH) .

* cited by examiner

*Primary Examiner*—Anita King
(74) *Attorney, Agent, or Firm*—Barry R. Lipsitz; Douglas M. McAllister

(57) ABSTRACT

In a holding device for a surgical instrument comprising a holder for the instrument, in order to enable pivotal movement of the instrument while avoiding simultaneous translational movement, it is proposed that the holder be held by at least two guide rods on a frame, the guide rods being rotably connected to the frame and to the holder, the bearing points of the guide rods on the holder being arranged in spaced relation to one another, and the spacing of the bearing points on the frame being greater than the spacing of the bearing points on the holder.

13 Claims, 5 Drawing Sheets

HOLDING DEVICE FOR A SURGICAL INSTRUMENT

Figure 1:
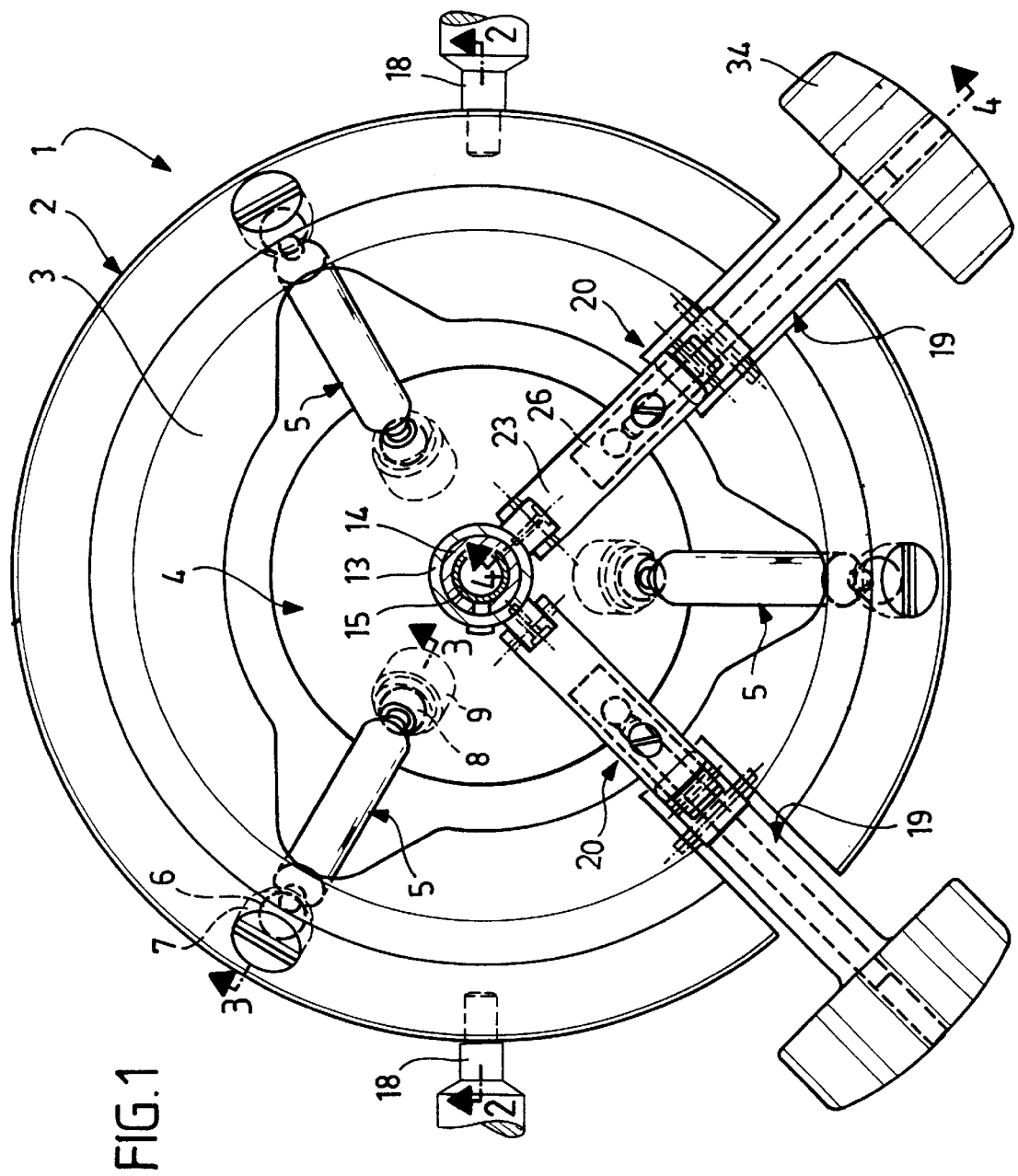

The present disclosure relates to the subject matter disclosed in German patent application No. 198 22 195.9 of May 16, 1998, the entire specification of which is incorporated herein by reference.

BACKGROUND OF THE INVENTION

The invention relates to a holding device for a surgical instrument comprising a holder for the instrument.

When performing operations it is often necessary to position surgical instruments in a certain position relative to the body and to fix the surgical instruments by means of a holder on the holding device which enables movement of the instrument relative to the holding device. For example, endoscopes have to be brought into different positions, etc.

When the instruments are guided through openings of the body, the problem arises, particularly when pivoting such instruments, that the instruments can only be pivoted through very small angles when the openings of the body are narrow, since the pivotal movement is limited by the size of the body opening.

The object of the invention is to so design a holding device of the generic kind that an instrument can be mounted at a spacing from an opening of the body in such a way as to be movable over a large pivot angle in spite of the expanse of the opening of the body being limited.

SUMMARY OF THE INVENTION

This object is accomplished with a holding device of the kind described at the beginning, in accordance with the invention, in that the holder is held via at least two guide rods on a frame, the guide rods being rotatably connected to the frame and to the holder, the bearing points of the guide rods on the holder being arranged at a spacing from one another, and the spacing of the bearing points on the frame being greater than the spacing of the bearing points on the holder.

Such a holding device design makes it possible to pivot the holder in the holding device along the path predetermined by the guide rods. An instrument mounted on the holder and directed at an opening of the body at a distance from the holder can then target this opening of the body during the entire movement of the holder as the holder is moved on a path which is essentially an approximation of the path of a circle or the surface of a sphere owing to the described kinematics. The center point of this circular path or spherical surface remains substantially unchanged, and if the holding device is arranged relative to the opening of the body in such a way that this center point lies in the region of the opening of the body, an instrument mounted on the holder can be positioned at a different angle of inclination such that its prolongation always runs through this center point and hence through the opening of the body. With each pivotal movement of the instrument, only the angle of inclination changes in the region of the center point, not the sideways position of the instrument, and, therefore, the pivotal movement is not impeded by the opening of the body or by the tissue surrounding the instrument in this region.

When within the scope of this invention, mention is made of a mounting of the holder via "guide rods", real guide rods are primarily being referred to, i.e., rod-shaped connecting elements between frame and holder. However, such guide members as movably guide a holder on the frame in such a way that the holder is guided relative to the frame so that the bearing points on the holder and on the frame which a real guide rod would assume are at a constant spacing from one another, even when these points are not connected to one another by real guide rods, also come under the term "guide rods". In an arrangement with two guide rods, i.e., in which the holder is only pivotable two-dimensionally, such a guidance of the holder could, for example, be realized by an orbital curve with which drivers on the holder match.

In this sense, the invention thus relates to real guide rods as well as to "virtual guide rods" which are defined solely by the constant spacing of the bearing points between which a real guide rod could engage.

It is crucial to the invention that owing to the special kinematics of the holder, a center point is created for the movement of the holder, which during all movements of the holder relative to the frame essentially maintains its position and is arranged at a spacing from the frame and from the holder so that the holding device can be placed on a patient's body in such a way that this unchangeable center point can be arranged at an opening of the body or inside the body where the holding device itself has no room.

Such a holding device could, for example, also be used to apply a beam with a different direction, for example, a laser beam, which is then incident in the region of this center point at a different angle but unmoved sideways.

Provision may, however, also be made for the surgical instrument to protrude on the side remote from the guide rods half-way between the bearing points on the holder beyond the line connecting the bearing points on the holder, i.e., for the instrument, seen from the holder, to approach this center point.

In particular, it is advantageous for the instrument to protrude at least so far out of the holder that it intersects a line which runs between the bearing points on the frame perpendicularly to their connecting lines. In other words, the instrument protrudes to such an extent out of the holder that it at least reaches the described center point.

It is expedient for the guide rods to be of the same length.

In a first embodiment, two guide rods are provided. Herein the movement of the holder is limited by guidance to a pivotal movement in the plane defined by the four bearing points. In this case, the holder can only be pivoted in one plane.

The guidance can, for example, be realized by the guide rods being pivotable at the bearing points about parallel axes which extend perpendicularly to the plane spanned by the bearing points.

In another embodiment, three guide rods are provided. These are cardanically mounted at the bearing points. The bearing points are offset uniformly along a circle in the circumferential direction. In such a construction, the holder can be pivoted in space. In this case, the holder moves approximately on a spherical surface and thus defines a center point which is identical in all positions of the holder.

It is expedient herein for the cardan mounting to be formed by a ball-and-socket joint mounting.

Provision is made in a preferred embodiment for the holder to carry a displacement device on which the instrument is displaceable along a line which runs between the bearing points perpendicularly to the lines connecting the bearing points on the holder. The instrument can thus be adjusted with respect to its spacing from the center point which remains the same. For example, the penetration depth of an endoscope is thereby adjustable.

In a preferred embodiment, the displacement device comprises a sleeve-type shaft which receives the instrument and is preferably held telescopically in a sleeve of the holder. In particular, the shaft can be screwable into the sleeve.

It is expedient for the frame to be of ring-shaped configuration.

In particular, provision may be made for the frame to comprise a side wall which surrounds the guide rods on the outside thereof and preferably widens in the shape of a funnel.

On the underside thereof, the frame can be closed off by the holder of plate-shaped construction.

In a particularly preferred embodiment, further provision is made for there to be mounted on the frame an adjustment device which displaces the holder relative to the frame along the paths predetermined by the guide rods and fixes it in any desired position.

For example, the adjustment device may comprise at least one toggle lever which is mounted at one end on the frame for pivotal movement about an axis of rotation and at its other end is connected in the manner of a swivel joint to the holder. By opening the toggle lever to a greater or lesser extent, the holder can be pivoted relative to the frame.

For this purpose, provision may be made for an adjusting member for changing the opening angle of the toggle lever to engage the two arms of the toggle lever. For example, the adjusting member may be a threaded spindle.

It is expedient for a grip of the adjusting member to protrude outwards from the frame.

For a holder which is pivotable in one plane only, a single toggle lever is adequate. For a holding device with three guide rods, which is thus pivotable in space, provision may, however, be made for two toggle levers to be arranged in planes extending transversely to one another and for the joints between the arms of each toggle lever to comprise two axes of rotation extending perpendicularly to one another. By virtue of such a design, an optional pivot angle in space can be preselected and fixed.

The following description of preferred embodiments of the invention serves in conjunction with the drawings to explain the invention in greater detail.

BRIEF DESCRIPTION OF THE INVENTION

Figure 2:
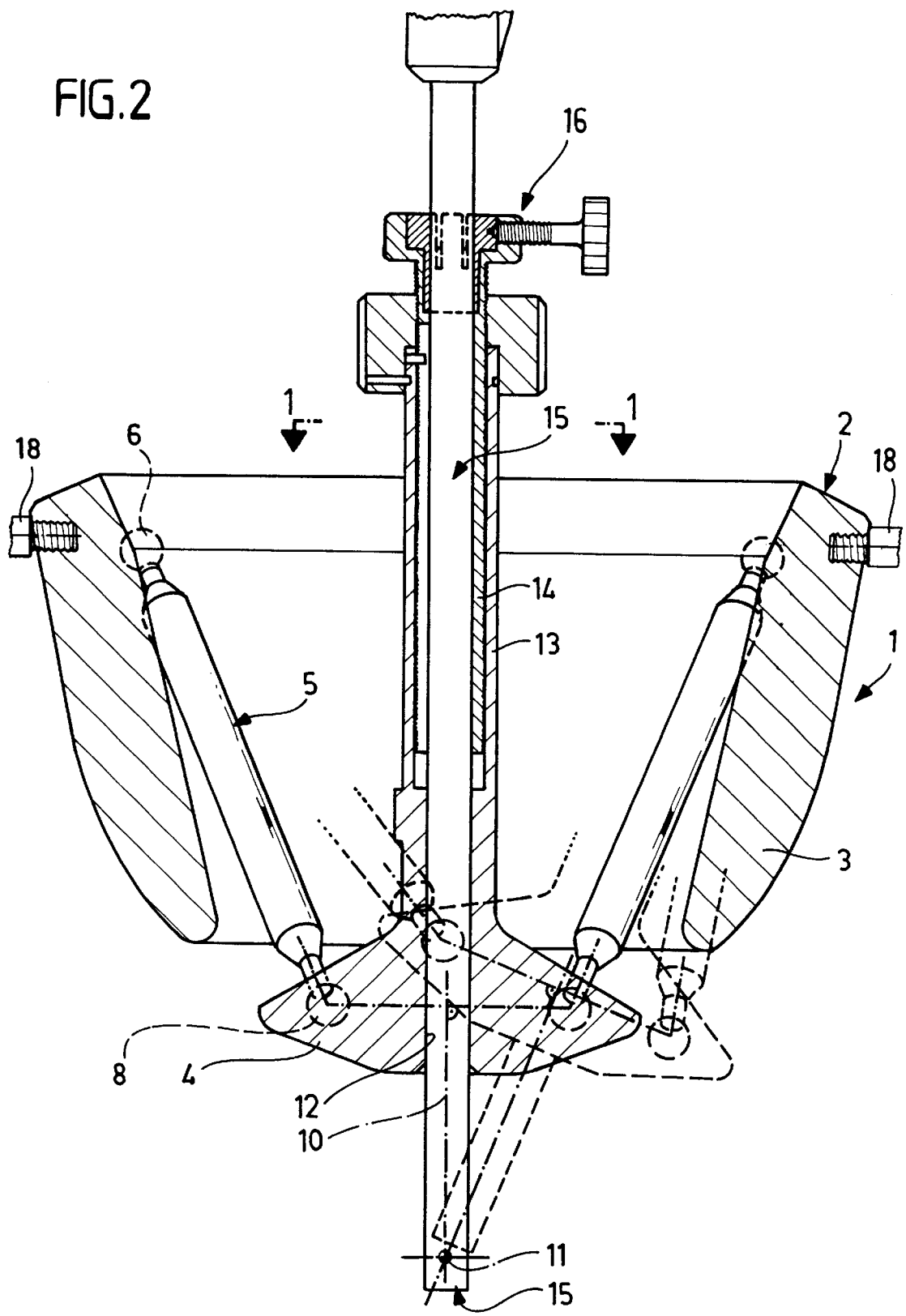
Figure 3:
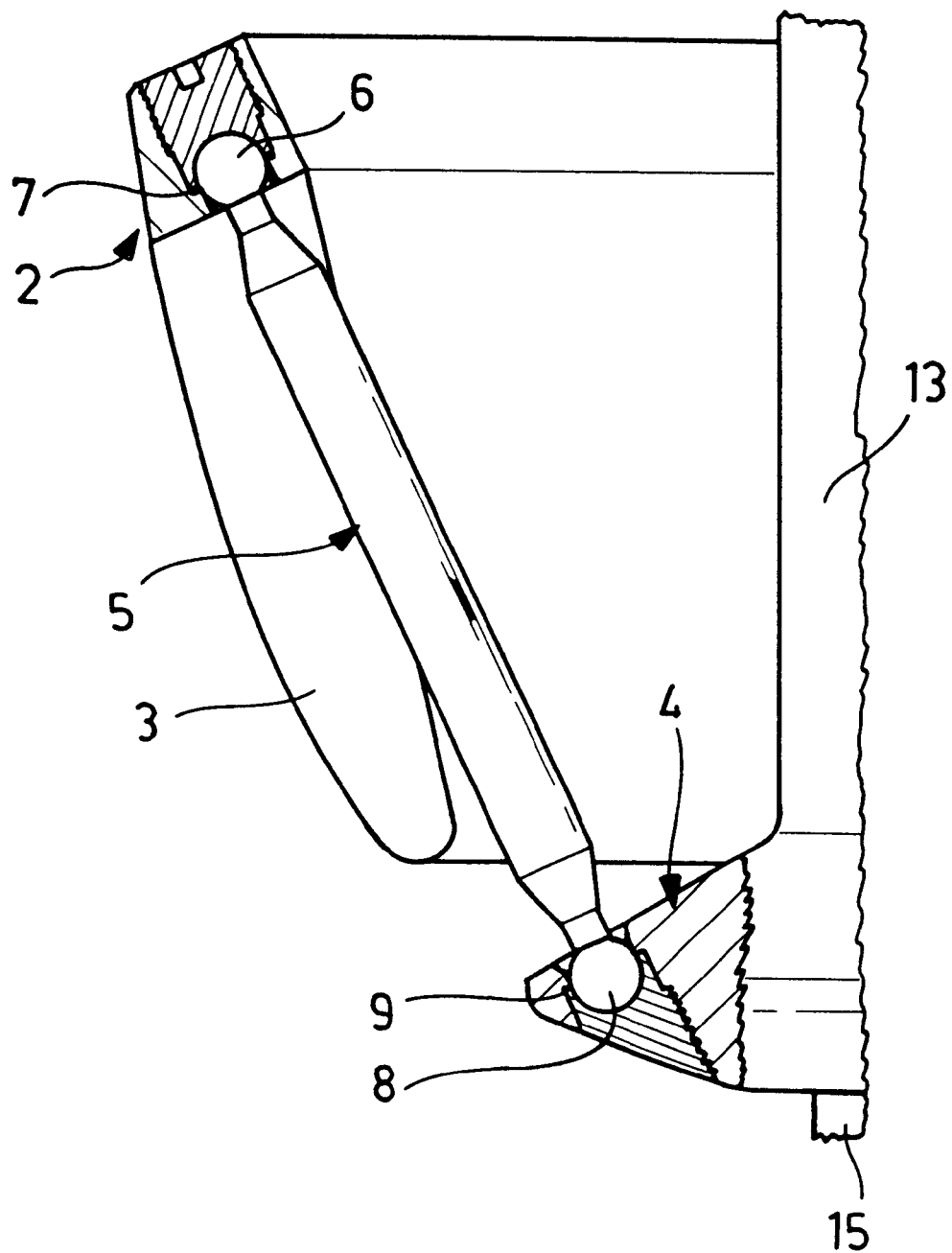
Figure 4:
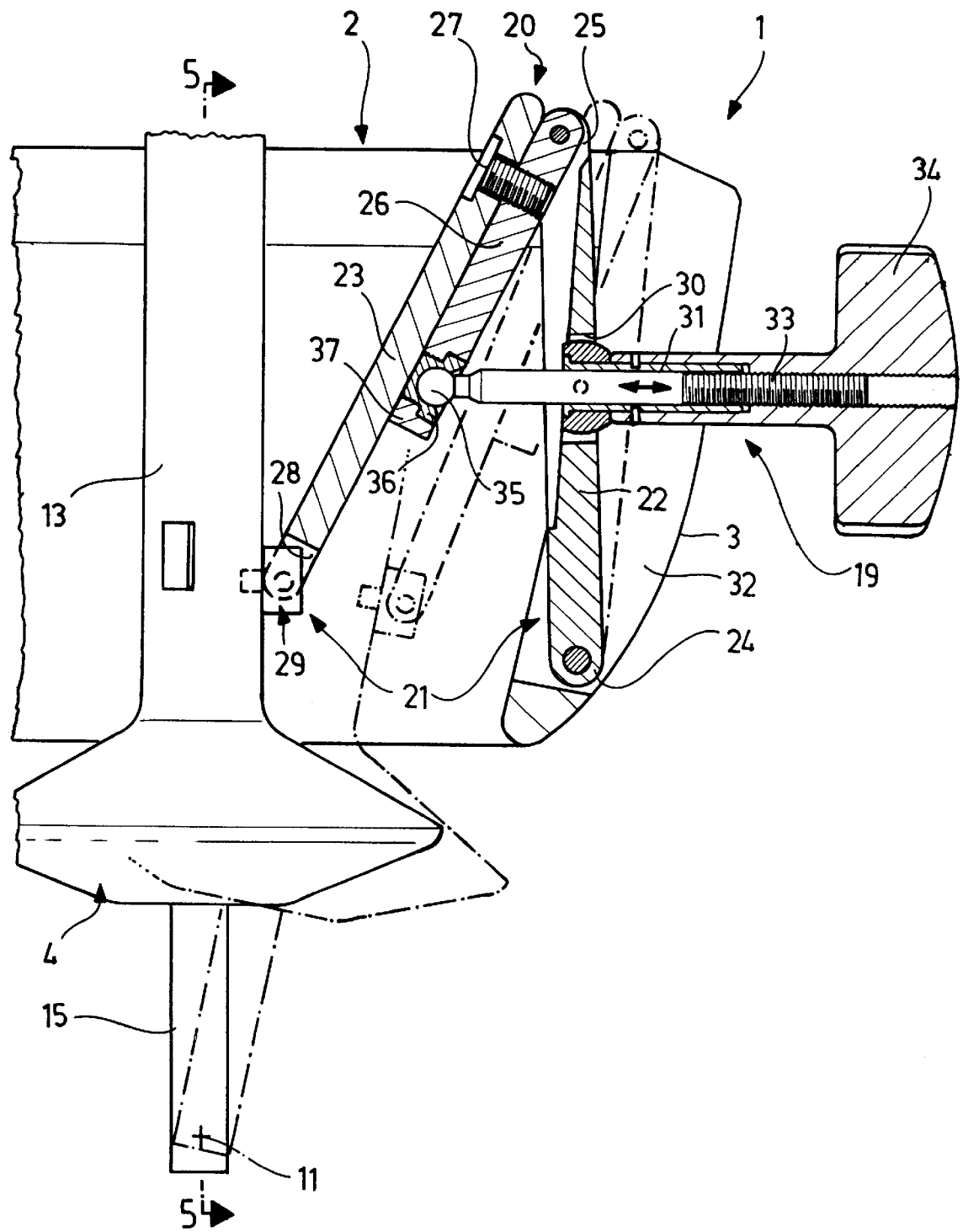

FIG. 1 a plan view of a holding device with three guide rods and two adjustment devices corresponding to a section taken along line 1—1 in FIG. 2;

FIG. 2 a sectional view taken along line 2—2 in FIG. 1;

FIG. 3 a sectional view taken along line 3—3 in FIG. 1;

FIG. 4 a sectional view taken along line 4—4 in FIG. 1; and

Figure 5:
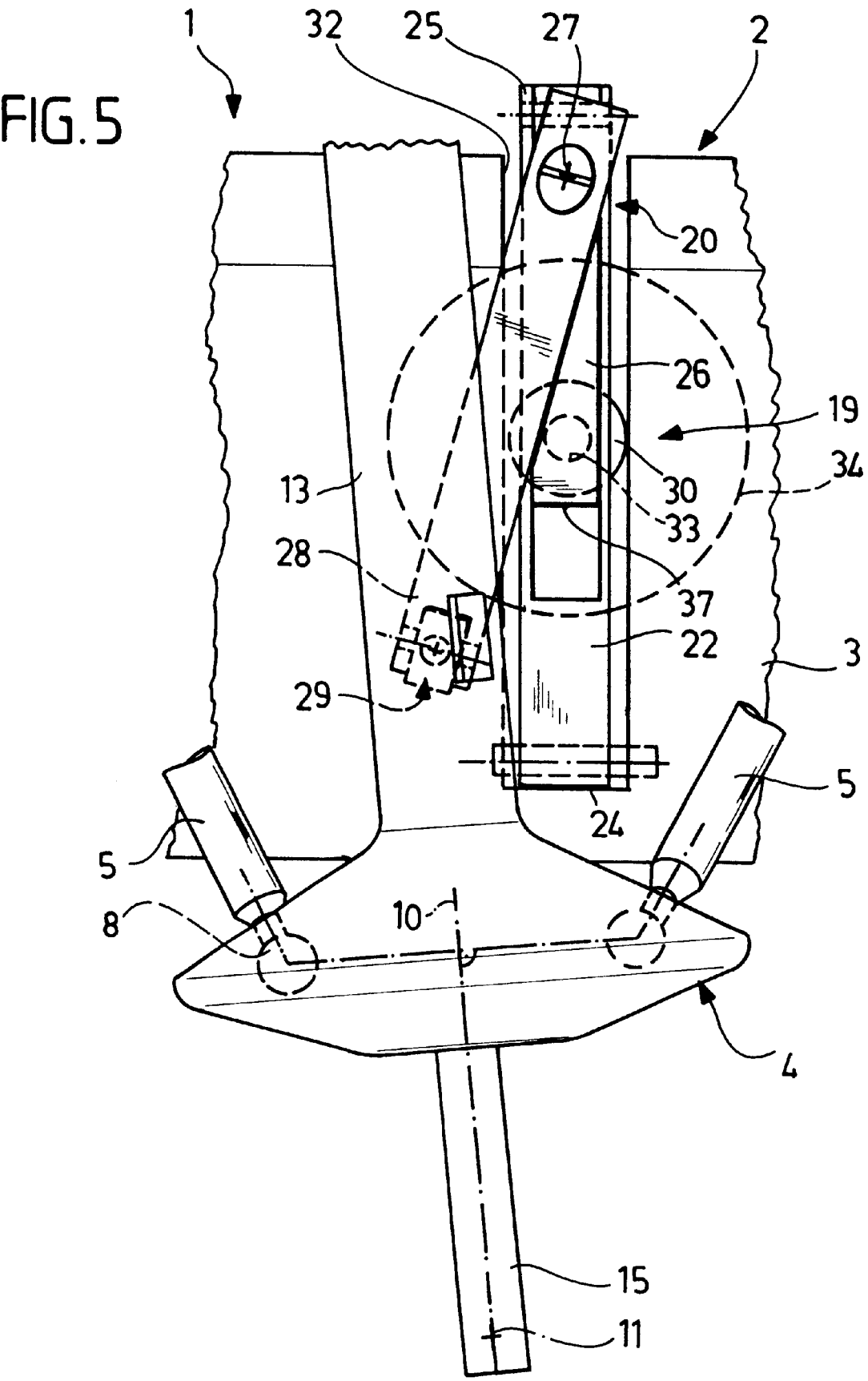

FIG. 5 a sectional view taken along line 5—5 in FIG. 4.

DETAILED DESCRIPTION OF THE INVENTION

The holding device 1 shown in the drawings comprises a frame 2 in the form of a side wall 3 closed in the shape of a ring and widening from the bottom to the top, and a disc-shaped or plate-shaped holder 4 which essentially closes the open underside of the frame 2. The holder 4 is connected to the top side of the frame 2 by three rod-shaped guide rods 5. The guide rods 5 are hung with a spherical head 6 in a bearing ring 7 at the top side of the frame 2 and are thus mounted for pivotal movement in all directions. Such bearing rings 7 are arranged at an angular spacing of 120° along the top side of the frame 2, and in a similar way the guide rods 5 engage by means of a spherical head 8 in a bearing ring 9 in the holder 4 (FIG. 3). The bearing rings 9 are also arranged on the holder 4 on a circle with a mutual angular spacing of 120°.

The circumference of the circle on which the bearing rings 7 of the frame 2 are located is larger than the diameter of the circle on which the bearing rings 9 of the holder 4 are located so that the guide rods 5 are inwardly inclined from the top to the bottom.

By virtue of the described mounting of the holder 4 on three guide rods 5, the holder 4 can be pivoted in all directions, and the center axis of the holder 4 which stands perpendicularly on the circle accommodating the bearing rings 9 and passes through the center point thereof can be pivoted within a cone whose tip lies at a center point 11 essentially unchanged in relation to the frame 2. This center point 11 lies on the longitudinal center axis of the frame 2 at a distance from the holder 4, i.e., on the side remote from the frame 2.

The possibilities of pivoting the holder 4 will be apparent from the illustration in FIG. 2 where the holder 4 is shown in a symmetrical center position in unbroken lines and in a sideways pivoted position in dot-and-dash lines. It is evident that the center axis 10 runs in both cases through the center point 11.

The holder 4 has a through-bore 12 extending concentrically in relation to the center axis 10 and continuing at the top side of the holder 4 into an elongate sleeve 13 into which a tubular shaft 14 is screwed. The shaft 14 protrudes at the top side out of the sleeve 13 and serves to receive a surgical instrument 15, for example, the shaft of an endoscope, which is fixed in the shaft 14 by a clamping device 16 and which extends through the sleeve 13 and through the through-bore 12 and projects downwards out of the holder 4, as a rule, at least as far as the center point 11. The size of the projection over the holder 4 may be varied by the shaft 14 being screwed to different depths into the sleeve 13.

By virtue of the described kinematics, the instrument 15 can be pivoted together with the holder 4 in various directions such that the instrument always passes approximately through the center point 11, i.e., such that in this region no sideways displacement of the instrument occurs, but only a change in the direction.

It is, therefore, possible to position the entire holding device 1 relative to the body such that at a desired location, for example, an opening of the body, only a change in direction is imparted to an instrument, but no sideways displacement. The positioning of the holding device 1 can be carried out by suitable means, for example, by a tripod-like device which engages the frame 2 by means of holding elements 18 at the sides.

In principle, the holder 4 could be mounted in the frame 2 so as to hang freely on the guide rods 5 and so the holder 4 is pivoted manually into different positions, as required, by the surgeon.

In the illustrated embodiment, an adjustment device 19 is, however, additionally provided with which it is possible to exactly adjust the position of the holder 4 in all directions and to then fix the position. This adjustment device 19 comprises two toggle lever arrangements 20 which are of identical design but which are arranged on the frame 2 offset through 90° about its longitudinal center axis. Only one of the two toggle lever arrangements 20 will be described in greater detail hereinbelow.

This comprises a toggle lever 21 with two arms 22, 23, whose outer arm 22 is mounted with its free end 24 at the lower end of the side wall 3 for rotation transversely about its longitudinal direction so that it is pivotable inwardly through about at the most 30° from a position extending approximately parallel to the side wall 3. Articulated at its other end 25 about an axis of rotation extending parallel to the axis of rotation at the free end 24 is a carrier 26 on whose outer side the inner arm 23 is mounted so as to extend parallel thereto, and, more particularly, so as to be rotatable about an axis of rotation 27 which is arranged in the area of the other end 25 and extends perpendicularly to the carrier 26 and to its axis of rotation in relation to the outer arm 22. At the free end 28, the inner arm 23 is connected in the manner of a swivel joint to the sleeve 13 of the holder 4 more particularly, by means of a cardan or spherical-head-type. Mounting 29 which enables rotation about two axes of rotation extending perpendicularly to one another.

The outer arm 22 comprises at the center thereof an opening 30 in which a threaded sleeve 31 is mounted on the outer arm 22 for rotation about an axis of rotation which extends parallel to the axis of rotation of the outer arm 22 at the free end thereof. The threaded sleeve 31 projects approximately perpendicularly outwards from the outer arm 22 and passes radially outwards through an opening 32 in the ring-shaped frame 2. Screwed into the threaded sleeve 31 is a threaded spindle 33 whose screw-in depth can be altered by a turning grip 34 connected in a rotationally fixed manner to the threaded spindle 33.

With a spherical-head-shaped end 35, the threaded spindle 33 engages a bearing bushing 36 at the free end 37 of the carrier 26 where it forms a swivel joint via which push and pull forces can be transmitted.

By screwing the threaded spindle 33 more or less deeply into the threaded sleeve 31, the opening angle of the two arms 22 and 23 of the toggle lever 21 can be adjusted, and this results in pivotal movement of the holder 4 about an axis of rotation which is essentially parallel to the axis of rotation of the outer arm 22 relative to the frame 2.

A corresponding pivotal movement of the holder 4 can be carried out by the two toggle lever arrangements 20 in planes extending perpendicularly to one another and so each pivotal position of the holder 4 relative to the frame 2 can be set in this way. Accordingly, the center axis of the holder 4 can be adjusted within the opening cone whose tip lies in the center point 11.

What is claimed is:

1. A holding device for a surgical instrument, comprising:
   a holder adapted to receive said instrument;
   a frame;
   at least two guide rods rotatably connected to said holder and to said frame, said guide rods having bearing points on said holder being arranged in spaced relation to one another and having bearing points on said frame being arranged in spaced relation to one another at a spacing greater than that of said bearing points on said holder;
   a displacement device carried on said holder adapted to displace said instrument along an imaginary line which runs between said bearing points on said holder perpendicularly to imaginary lines connecting said bearing points on said holder, said displacement device comprising a sleeve-type shaft adapted to receive said instrument.

2. The holding device in accordance with claim 1, wherein said shaft is telescopically held in a sleeve of said holder.

3. The holding device in accordance with claim 2, wherein said shaft is screwable into said sleeve.

4. The holding device in accordance with claim 1, wherein said frame is of ring-shaped construction.

5. The holding device in accordance with claim 4, wherein said frame comprises a side wall surrounding said guide rods on the outside thereof.

6. The holding device in accordance with claim 5, wherein:
   said holder is a plate-shaped holder; and
   said frame is closed off on an underside by said plate-shaped holder.

7. The holding device in accordance with claim 1, wherein an adjustment device mounted on said frame displaces said holder relative to said frame along paths predetermined by said guide rods and fixes said holder in an optional position.

8. A holding device for a surgical instrument, comprising:
   a holder adapted to receive said instrument;
   a frame;
   at least two rigid guide rods rotatably connected directly to said holder and to said frame, said guide rods having bearing points on said holder being arranged in spaced relation to one another and having bearing points on said frame being arranged in spaced relation to one another at a spacing greater than that of said bearing points on said holder; and
   an adjustment device mounted on said frame and connected to said holder for displacing said holder relative to said frame along paths predetermined by said guide rods and fixing said holder in an optional position.

9. The holding device in accordance with claim 8, wherein said adjustment device comprises at least one toggle lever having an inner arm and an outer arm, one end of said outer arm being mounted on said frame for pivotal movement about an axis of rotation and one end of said inner arm being connected in the manner of a swivel joint to said holder.

10. The holding device in accordance with claim 9, wherein:
    the at least two guide rods comprise three guide rods;
    two toggle levers are arranged in planes extending transversely to one another, each toggle lever having two arms; and
    joints between said arms comprise two axes of rotation extending perpendicularly to one another.

11. The holding device in accordance with claim 9, wherein an adjusting member for changing an opening angle of said toggle lever engages the inner arm and the outer arm of said toggle lever.

12. The holding device in accordance with claim 11, wherein said adjusting member is a threaded spindle.

13. The holding device in accordance with claim 11, wherein a grip of said adjusting member protrudes outwards from said frame.

* * * * *